US008841258B2

(12) United States Patent
DeLano et al.

(10) Patent No.: US 8,841,258 B2
(45) Date of Patent: Sep. 23, 2014

(54) METHODS TO ACCELERATE TISSUE AND WOUND HEALING RATES AND REDUCE SWELLING AND SCAR FORMATION

(75) Inventors: Frank A. DeLano, San Diego, CA (US); Geert W. Schmid-Schonbein, Del Mar, CA (US)

(73) Assignee: The Regents of The University of California, Oakland, CA (US)

( * ) Notice: Subject to any disclaimer, the term of this patent is extended or adjusted under 35 U.S.C. 154(b) by 0 days.

(21) Appl. No.: 13/505,722

(22) PCT Filed: Sep. 28, 2010

(86) PCT No.: PCT/US2010/050600
§ 371 (c)(1),
(2), (4) Date: Aug. 17, 2012

(87) PCT Pub. No.: WO2011/038417
PCT Pub. Date: Mar. 31, 2011

(65) Prior Publication Data
US 2012/0309693 A1 Dec. 6, 2012

Related U.S. Application Data

(60) Provisional application No. 61/246,527, filed on Sep. 28, 2009.

(51) Int. Cl.
| A61K 38/57 | (2006.01) |
| A61K 31/337 | (2006.01) |
| A61K 31/215 | (2006.01) |
| A61K 31/235 | (2006.01) |
| A61K 31/365 | (2006.01) |
| A61K 45/06 | (2006.01) |
| A61K 31/24 | (2006.01) |
| A61K 31/195 | (2006.01) |

(52) U.S. Cl.
CPC ............... *A61K 38/57* (2013.01); *A61K 31/365* (2013.01); *A61K 45/06* (2013.01); *A61K 31/24* (2013.01); *A61K 31/195* (2013.01)
USPC ........... 514/20.3; 514/20.1; 514/1.1; 514/2.3; 514/2.4

(58) Field of Classification Search
CPC . A61K 9/0012; A61K 9/0053; A61K 31/195; A61K 31/215; A61K 31/365; A61K 38/005; A61K 38/57; A61K 38/55; A61K 38/16; A61K 45/06; C12N 2009/00
See application file for complete search history.

(56) References Cited

U.S. PATENT DOCUMENTS

| 6,344,189 | B1 * | 2/2002 | Bunn et al. ............... 424/78.06 |
| 6,534,283 | B1 * | 3/2003 | Schmid-Schoenbein et al. ................... 435/23 |
| 2006/0057111 | A1 | 3/2006 | Hedlund et al. |
| 2007/0142337 | A1 * | 6/2007 | Schmid-Schonbein et al. ................... 514/152 |
| 2007/0294107 | A1 | 12/2007 | Schmid-Schonbein et al. |
| 2010/0179091 | A1 | 7/2010 | Schmid-Schonbein |
| 2010/0303799 | A1 | 12/2010 | Schmid-Schonbein |
| 2011/0039781 | A1 | 2/2011 | Schmid-Schonbein |

FOREIGN PATENT DOCUMENTS

| WO | WO2009/045543 | 4/2009 |
| WO | WO2009/132149 | 10/2009 |
| WO | WO2011/038417 | 3/2011 |

OTHER PUBLICATIONS

Liesenfeld et al., 2006 Wound Healing Society, Poster #89, retrieved from http://content.stockpr.com/qmdt/media/d166915d079a967f12e6c9f114cb0ab1.pdf on Mar. 17, 20134.*
Rieder et al., Gut (2007) 56, 130-139, retrieved from http://www.ncbi.nlm.nih.gov/pmc/articles/PMC1856649/ on Mar. 17, 2013.*
Deitch E A, Shi H P, Lu Q, et al. "Serine proteases are involved in the pathogenesis of trauma-hemorrhagic shock-induced gut and lung injury." Shock. 2003; 19:452-456.
Fitzal F, DeLano F A, Young C, Rosario H S, Junger W G, Schmid-Schonbein G W. "Pancreatic enzymes sustain systemic inflammation after an initial endotoxin challenge", Surgery, 134:1-11, 2003.
Madan et al., "Use of Ciprofloxacin in the Treatment of Hospitalized Patients with Intra-abdominal Infections", Clinical Therapeutics 26(10):1564-77, 2004.
Penn, A H, Hugli, T E, Schmid-Schonbein, G W. "Pancreatic enzymes generate cytotoxic mediators in the intestine", Shock 27(3):296-304, 2007.
Schmid-Schonbein G W. 2008 Landis Award lecture—Inflammation and the Autodigestion Hypothesis. Microcirculation, 2009; 16:289-306.
Wiseman et al., "The Effect of Tranexamic Acid in Fibrin Sealant on Adhesion Formation in the Rat," J Biomed Mater Res Part B: Appl Biomater 68B:222-30, 2004.

* cited by examiner

*Primary Examiner* — Karlheinz R Skowronek
*Assistant Examiner* — Catherine Mader
(74) *Attorney, Agent, or Firm* — Sughrue Mion, PLLC

(57) ABSTRACT

The present disclosure serves to reduce the healing time of tissue wounds, including those formed during surgery, whether necessary or elective (including cosmetic surgery), by providing a therapeutic dose of a pancreatic enzyme inhibitor.

15 Claims, 1 Drawing Sheet

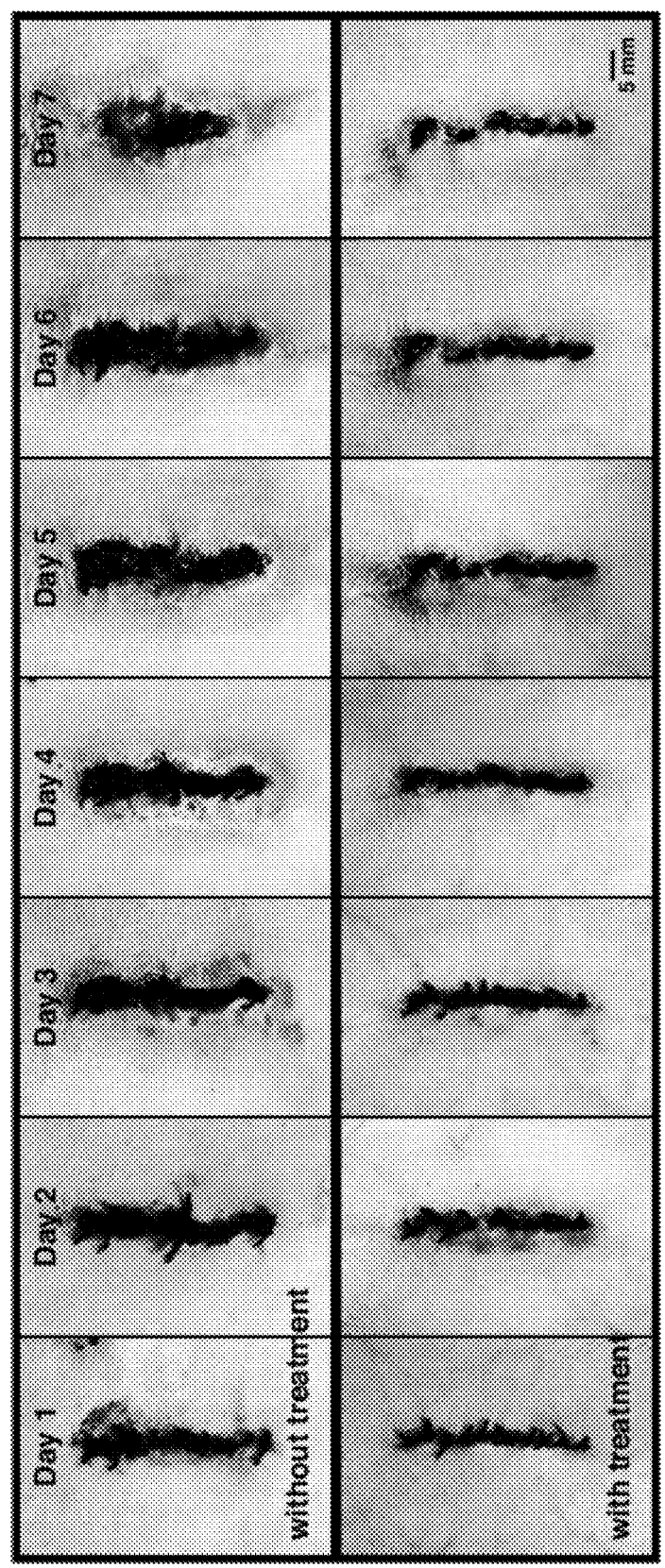

METHODS TO ACCELERATE TISSUE AND WOUND HEALING RATES AND REDUCE SWELLING AND SCAR FORMATION

This application is a U.S. National Stage Application under 35 U.S.C. 371 of the PCT application with Ser. No. PCT/US2010/050600, filed Sep. 28, 2010; which claims priority to U.S. Provisional Patent Application Ser. No. 61/246,527, filed Sep. 28, 2009, the contents of which are hereby incorporated by reference herein in their entirety into this disclosure.

BACKGROUND OF THE INVENTION

1. Field of the Invention

The present invention relates to treatment procedures. In particular, the present invention relates to methods to accelerate tissue and wound healing rates and reduce swelling and scar formation.

2. Background of the Invention

Skin wounds are one of the most common injuries in humans and animals of all ages, whether caused by accidents, disease or surgery. In humans, such wounds are often conventionally treated with surface antibiotics and many different forms of bandages, often but not always enriched with antibiotics and growth factors. There are numerous wound healing agents currently on the market. Some of the wound healing agents applied to the surface of tissues include, for example:

Hydrocolloid dressings
Hydrogel dressings
Foam dressings
Calcium Alginate dressings
Collagen dressings
Silicone gel sheeting
Compression dressings
Charcoal dressings Although the variety of wound healing agents is numerous, each has some drawbacks and disadvantages, whether they are specificity of wounds they heal, reactivity or other side effects. For example, hydrocolloid dressings (consists of absorptive ingredients, typically carboxymethycellulose, pectin or gelatin) are used frequently, but cannot be used if the wound or surrounding skin is infected. Another common end result is the resultant scar left after the healing of the wound.

Thus, although there are a large number of ways in which wounds may be typically treated, each has its own characteristic setbacks. Thus, there exists a need in the art for new methods of treating tissues and wounds. The methods should be simple to administer, effective and capable of reducing swelling and scar formation.

SUMMARY OF THE INVENTION

The present invention serves to reduce the healing time of tissue wounds, including those formed during surgery, whether necessary or elective (including cosmetic surgery). The invention is based on a the discovery that pancreatic digestive enzymes—that are normal part of daily digestion—leak during a number of situations, such as for example, injuries, surgery, general anesthesia, and during caloric overconsumption into the intestine, from the lumen of the intestine and the pancreas into the lymphatics and systemic circulation and interfere with normal would healing by destruction of immune cell functions and direct injury to cells (neutrophils, macrophages, stem cells) that are part of the would healing process. Blockade of the digestive enzymes serves to attenuate the degrading action of these enzymes, enhance the normal immune functions and signaling processes that are required for removal of old cell debris and generation of new tissue and angiogenesis and therefore enhance wound healing.

The digestive enzymes can enter into the abdominal lymphatic system and cause major damage to the abdominal lymph node system (B-, T-lymphocytes, macrophages, dendritic cells) and reduce the ability to mount an adaptive immune defense or wound healing in the lymphoid system, predisposing it to lymphatic fluid leakage and tissue swelling.

Thus, the present invention provides a better alternative to treating wounds than conventional method wherein in certain examples such as at skin closure sites, methods according to the present invention result in reduced redness, swelling, exudates amount, tissue indurations, and scab formation around the incision site, as compared to untreated controls.

In one exemplary embodiment, the present invention is a method for accelerating tissue healing. The method includes administering to an individual a therapeutic dose of a pancreatic enzyme inhibitor.

In another embodiment, the present invention is a method for accelerating wound healing. The method includes administering to an individual a therapeutic dose of a pancreatic enzyme inhibitor.

In another embodiment, the present invention is a method for reducing swelling. The method includes administering to an individual a therapeutic dose of a pancreatic enzyme inhibitor.

In yet another embodiment, the present invention is a method for reducing scar formation and fibrosis. The method includes administering to an individual a therapeutic dose of a pancreatic enzyme inhibitor.

BRIEF DESCRIPTION OF THE DRAWINGS

FIG. 1 shows an image progression of wound healing stages for seven consecutive postoperative days after induction of cecal peritonitis without and with treatment using compound FAD1125.

DETAILED DESCRIPTION OF THE INVENTION

The present invention serves to reduce the healing time of tissue wounds, including those formed during surgery, whether necessary or elective (including cosmetic surgery). Methods according to the present invention serve to restore defective cellular wound healing functions that are compromised in the presence of degrading digestive enzymes and by the cytotoxic mediators that produce for example in the intestine (e.g. cytotoxic unbound free fatty acids) by receptor cleavage and direct cytotoxic activities of tissue fragments generated by digestive enzymes. Thus, the present invention provides a better alternative to treating wounds than conventional method wherein in certain examples such as at skin closure sites, methods according to the present invention result in reduced redness, swelling, exudates amount, tissue indurations, and scab formation around the incision site, as compared to untreated controls.

The present invention provides for treatment which is novel and unique since it serves to attenuate proteolytic activity that impairs wound healing. The treatment addresses specifically a source of proteolytic activity, which is derived from the digestive enzymes in the intestine and the pancreas. The treatment works through a separate pathway and possibly in addition to traditional enhancements of wound healing.

In surgery, administration (or pre-administration) of a pancreatic enzyme inhibitor may be conducted directly into the lumen of the intestine (by oral administration, introduction via an esophageal catheter, direct injection into the lumen of the intestine during surgery). The agents which may be used are, individually or in combination:

FUTHAN, nafamostat mesilate (or the order of 0.1 mM)

TRASYLOL, aprotinin (Bayer) (1.4 mg/ml), serine protease inhibitor orlistat (5 to 50 mg/ml), lipase inhibitor CYCLOKAPRON, tranexamic acid (on the order of 0.1 mM) or any other pancreatic enzyme, serine protease or serpin inhibitor. For example, any one or more of the following may be used: FUTHAN nafamostat mesilate, FOY gabexate mesilate, camostate mesilate, TRASYLOL aprotinin, orlistat, CYCLOKAPRON tranexamic acid, apha 1 antitrypsin, or any other trypsin, chymotrypsin, elastase or serine or serpin protease inhibitor.

The amount, volume and/or rate administered are adjusted according to intestine size to achieve blockade of digestive enzyme activity, and would be readily apparent to one having ordinary skill in the art after consideration of the present disclosure.

In certain exemplary embodiments, the present invention is effective by administration of the enzyme inhibitors directly into the peritoneum. This applies to any case in which there is an indication that digestive enzymes may have leaked across the intestinal wall (e.g. appendicitis, puncture wounds). The protease inhibition may also be combined with an antibiotic to kill possible bacteria that leaked into the peritoneum.

The protease inhibitors can also be combined with inhibitors for pancreatic amylase and lipases, as supplement.

In situations in which pancreatic digestive enzymes are detected also in the circulation, the enteral administration can also be supplemented with the present technique.

In elective surgery, the inhibitor may be administered prior to general anesthesia/surgery as pretreatment. In non-elective surgery, the inhibitor may be administered as early as practical, including in some instances during post surgery.

The present invention and its discovery are based on direct observations in rodent experiments involving skin wound closures. FIG. 1 shows an image progression of wound healing stages for seven consecutive postoperative days after induction of cecal peritonitis without and with treatment using a compound FAD1125. The figure clearly shows that without treatment, the wound healing was not as effective as with treatment. At day 7, the treated wound shows clear accelerated healing while the untreated wound shows some healing but not to the extent of the treated wound. Thus, there is a significant effect on wound acceleration and healing rates according to the present invention.

The methods according to the present invention have application to any surgical situation involving general anesthesia, including any form of traditional elective and non-elective surgery, robotic surgery, surgery involving skin and non-skin incisions, (e.g., cosmetic surgery, transplantations, including bone marrow transplantations, stem cell treatments, gene therapy, radiation and burn injuries), abdominal and non-abdominal surgery, and others.

Further, the present methods could also work in chronic non-healing wounds (e.g., ulcers), skin- and other tissue-lesion, amputations, or in any in- and out-patient wound treatment, The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method for accelerating tissue healing in an individual, the method comprising:
    administering into the lumen of the intestine of the individual a therapeutic dose of a composition comprising a pancreatic enzyme inhibitor and an antibiotic, wherein the tissue is of a skin incision closure site, thereby accelerating tissue healing.

2. The method of claim 1, wherein the administration is oral.

3. The method of claim 1, wherein the administration is via an esophageal catheter.

4. The method of claim 1, wherein the administration is via direct injection into the lumen of the intestine.

5. The method of claim 1, wherein the pancreatic enzyme inhibitor comprises protease inhibitors.

6. The method of claim 1, wherein the pancreatic enzyme inhibitor comprises one or more of futhane, foy, camostate mesilate, trasylol, orlestat, cycklokapron, apha 1 antitrypsin, or any other trypsin, chymotrypsin, elastase or serine protease inhibitor.

7. The method of claim 1, wherein the administration occurs prior to general anesthesia for elective surgery or emergency surgery.

8. A method for accelerating wound healing in an individual, the method comprising:
    administering into the lumen of the intestine of the individual a therapeutic dose of a composition comprising a pancreatic enzyme inhibitor and an antibiotic, wherein the wound is a skin incision closure site, thereby accelerating wound healing.

9. The method of claim 8, wherein the administration is oral.

10. The method of claim 8, wherein the administration is via an esophageal catheter.

11. The method of claim 8, wherein the administration is via direct injection into the lumen of the intestine.

12. The method of claim 8, wherein the pancreatic enzyme inhibitor comprises protease inhibitors.

13. The method of claim 8, wherein the pancreatic enzyme inhibitor comprises one or more of futhane, foy, camostate mesilate, trasylol, orlestat, cycklokapron, apha 1 antitrypsin, or any other trypsin, chymotrypsin, elastase or serine protease inhibitor.

14. The method of claim 8, wherein the administration occurs prior to general anesthesia for elective surgery or emergency surgery.

15. The method of claim 8, wherein the administration further comprises pancreatic amylase inhibitors and lipase inhibitors.

\* \* \* \* \*